US008940791B2

(12) United States Patent
Chandran

(10) Patent No.: US 8,940,791 B2
(45) Date of Patent: *Jan. 27, 2015

(54) ACETYLATED AMINO ACIDS AS ANTI-PLATELET AGENTS, NUTRITIONAL AND VITAMIN SUPPLEMENTS

(75) Inventor: V. Ravi Chandran, Allen, TX (US)

(73) Assignee: Signature R&D Holdings, LLC, Allen, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/183,013

(22) Filed: Jul. 14, 2011

(65) Prior Publication Data
US 2011/0275713 A1 Nov. 10, 2011

Related U.S. Application Data

(63) Continuation of application No. 11/598,425, filed on Nov. 13, 2006, now Pat. No. 8,003,683.

(60) Provisional application No. 60/735,280, filed on Nov. 11, 2005.

(51) Int. Cl.
A01N 37/02 (2006.01)
A61K 31/40 (2006.01)
A23L 1/305 (2006.01)
A61K 31/198 (2006.01)
A61K 31/22 (2006.01)
A61K 31/221 (2006.01)
A61K 31/223 (2006.01)
A61K 31/401 (2006.01)
A61K 31/4015 (2006.01)
A61K 31/4365 (2006.01)
A61K 31/519 (2006.01)
A61K 31/616 (2006.01)
A61K 45/06 (2006.01)
C07K 5/02 (2006.01)
C07K 5/062 (2006.01)
C07K 5/065 (2006.01)
C07K 5/078 (2006.01)
A23L 2/52 (2006.01)
A61K 31/222 (2006.01)
A61K 38/00 (2006.01)

(52) U.S. Cl.
CPC .............. A61K 31/40 (2013.01); A23L 1/3051 (2013.01); A61K 31/198 (2013.01); A61K 31/22 (2013.01); A61K 31/221 (2013.01); A61K 31/223 (2013.01); A61K 31/401 (2013.01); A61K 31/4015 (2013.01); A61K 31/4365 (2013.01); A61K 31/519 (2013.01); A61K 31/616 (2013.01); A61K 45/06 (2013.01); C07K 5/0205 (2013.01); C07K 5/06026 (2013.01); C07K 5/0606 (2013.01); C07K 5/06069 (2013.01); C07K 5/06078 (2013.01); C07K 5/06165 (2013.01); A23L 2/52 (2013.01); A61K 31/222 (2013.01); A23V 2002/00 (2013.01); A61K 38/00 (2013.01)
USPC .......................................... 514/548; 514/547

(58) Field of Classification Search
CPC ..... A61K 31/22; A61K 31/135; A61K 31/222; C07C 69/017
USPC .................................................. 514/548, 547
See application file for complete search history.

(56) References Cited

U.S. PATENT DOCUMENTS

| 2,349,774 | A | * | 5/1944 | Toennies ........................ 548/532 |
| 3,932,638 | A | | 1/1976 | Coirre et al. |
| 3,997,559 | A | | 12/1976 | Coirre et al. |
| 4,268,524 | A | | 5/1981 | Cavazza |
| 4,340,592 | A | | 7/1982 | Adibi |
| 4,704,285 | A | | 11/1987 | Alderman |
| 5,036,052 | A | | 7/1991 | Ozeki et al. |
| 5,431,904 | A | | 7/1995 | Laney |
| 5,432,183 | A | | 7/1995 | Schulte |
| 5,827,874 | A | | 10/1998 | Meyer et al. |
| 6,706,892 | B1 | | 3/2004 | Ezrin et al. |
| 6,770,660 | B2 | | 8/2004 | DiBattiste et al. |
| 2002/0099013 | A1 | | 7/2002 | Piccariello et al. |
| 2002/0146783 | A1 | | 10/2002 | Maier et al. |
| 2005/0031547 | A1 | | 2/2005 | Tamarkin et al. |
| 2006/0063827 | A1 | | 3/2006 | Yu et al. |
| 2006/0287244 | A1 | | 12/2006 | Chandran |

FOREIGN PATENT DOCUMENTS

| EP | 0 308 278 A1 | 3/1989 |
| GB | 2 013 495 A | 8/1979 |
| GB | 2 171 302 A | 12/2012 |

(Continued)

OTHER PUBLICATIONS

Hogan J.C. et al., "Glyceryl trinitrate and platelet aggregation: effects of N-acetyl-cysteine", Br. J. clin. Pharmac. 27:617-619 (1989).
A. Previero et al., "Specific O-Acylation of Hydroxylamino Acids in Presence of Free Amino Groups." Biochimica et Biophysica Acta, 7-13; 2 (1972).
Barkdoll A.E. et al., "Syntheses at Tyrosyltyrosyltyrosine and Tyrosyltyrosyltyrosyltrosine." Journal of the American Chemical Society, 66, 951-963: 3 (1944).
Sakami et al., "The Investigation of Amino Acid Reactions by Methods of Non-Aqueous Titrimetry." Journal of Biological Chemistry, 144-203; 4 (1942).
Chong Heng et al., Mechanism of Nasal Absorption of Drugs II: Absorption of L-Tyrosine and the Effect of Structural Modification on its Absorption. Journal of Pharmaceutical Science, 74(12), 1298-1301 (1985).
Fleisher, D., et al., "Improved oral drug delivery solubility limitations overcome by the use of prodrugs", Advanced Drug Delivery Reviews, 19:115-130 (1996).
Korean Office Action dated Apr. 26, 2012 issued in Application No. 10-2006-7002214 with English language translation.

(Continued)

Primary Examiner — Jason Sims
Assistant Examiner — Ibrahim D Bori
(74) Attorney, Agent, or Firm — Scully, Scott, Murphy & Presser, P.C.

(57) ABSTRACT

This invention relates to pharmaceutical compounds and nutritional supplements that are acetylated derivatives of naturally occurring amino acids and acetylated derivatives of peptides derived from naturally occurring amino acids containing hydroxyl groups. They are as useful as anti-platelet drugs, and as nutritional supplements.

20 Claims, 2 Drawing Sheets

(56) References Cited

FOREIGN PATENT DOCUMENTS

| JP | 54-113442 A | 9/1979 |
|---|---|---|
| JP | 2001-206897 A | 7/2001 |
| JP | 2002-262896 A | 9/2002 |
| JP | 2005-247841 A | 9/2005 |
| JP | 2006-143649 A | 6/2006 |
| WO | 95/07069 A1 | 3/1995 |
| WO | 2004/080468 A1 | 9/2004 |

OTHER PUBLICATIONS

Database WPI XP-002702908, Week 200171, Thomson Scientific.
Postiglione, A., et al. "Effect of Acute Administration of L-Acetyl Carnitine on Cerebral Blood Flow in Patients With Chronic Cerebral Infarct", Pharmacological Research, vol. 23, No. 3, Apr. 1, 1991, pp. 241-246.
European Search Report from corresponding European Application No. 06 82 7756.5 dated Jul. 29, 2013.
Drugs.com, http://www.drugs.com/condition/platelet-aggregation-inhibition.html?printable=1, "Platelet Aggregation Inhibition Medications" accessed Feb. 23, 2012.
Han, B., et al., "Comparative Study on Teh Effect of Acetylcar-Nitine and Carnitine on Experimental Hyposiac Heart Failure and Their Interactions With Strophanthin K", Acta Pharmaccutica Sinica 20(8):606-609 (1985) (English language abstract).
Lewis, G.P. et al., "Isolation and identification of pharmacologically active amino acids in skin and their structure-activity relationship on the guinea-pig ileum", Br. J. Pharmac. 45:104-117 (1972).
Wikipedia.com, http://en.eikipedia.org/wiki/Antiplatelet_drug, "Antiplatelet drug", accessed Feb. 23, 2012.
Wikipedia.com, http://en.wikipedia.org/wiki/Platelet, "Platelet", accessed Feb. 23, 2012.
Partial European Search Report issued in Application No. EP 14 15 6764 dated Aug. 21, 2014.
Kido, Y., et al. "Functional relevance of carnitine transporter OCTN2 to brain distribution of L-carnitine and acetyl-L-carnitine across the blood-brain barrier" Journal of Neurochemistry 79:959-969 (2001).
Kwon, O., et al. "HPLC Determination and Pharmacokinetics of Endogenous Acetyl-L-Carnitine (ALC) in Human Volunteers Orally Administered a Single Dose of ALC" Arch Pharm Res 27(6):676-681 (2004).
Inano, A., et al., "Acetly-L-carnitine Permeabiligy across the Blood-Brain Barrier and Involvement of Carnitine Transporter OCTN2" Biopharmaceutics and Drug Disposition 24:357-365 (2003).
Partial European Search Report dated Nov. 26, 2014 issued in European Application No. 14 15 6764.
European Search Report dated Dec. 12, 2014 issued in European Application No. 14 15 6764.

\* cited by examiner

ACETYLATED AMINO ACIDS AS ANTI-PLATELET AGENTS, NUTRITIONAL AND VITAMIN SUPPLEMENTS

CROSS REFERENCE TO RELATED APPLICATION

The present application is a continuation of co-pending application U.S. Ser. No. 11/598,425 filed Nov. 13, 2006, which is claiming benefit of provisional US application having U.S. Ser. No. 60/735,280, filed on Nov. 11, 2005.

BACKGROUND OF THE INVENTION

Anti-platelet drugs are useful in the treatment of cardiovascular and cerebrovascular diseases. They have been shown to reduce the incidence of vascular events, most importantly, Myocardial Infarction (MI) and stroke. Older people are particularly vulnerable to these diseases, and their risk factors increase with age.

Anti-platelet drugs reduce the aggregation of platelets in the blood, which if left untreated in an atherosclerotic blood vessel, may lead to thromboembolism formation and subsequent cardiovascular events such as stroke or MI. Atherosclerosis is the major cause of vascular events. It can be manifested as coronary disease, cardiovascular disease or peripheral vascular disease (PVD), and some patients suffer from more than one form of the multiple diseases stated above.

It has been shown that fatty deposits found inside the arterial vessels of some asymptomatic individuals as young as 10 years old may later become the site of formation of the atherosclerotic plaques. These plaques are prone to rupture, exposing thrombogenic substances that undergo a cascade of reactions, leading to the formation of a thrombus, which can lead to occlusion of a blood vessel, leading potentially to MI or stroke.

A thrombus is an abnormal clot that develops in blood vessels. Blood flow past the clot likely causes the clot to break away from its attachment to the blood vessel. These freely flowing clots are known as emboli. The emboli do not stop flowing until they plug a narrow portion in the circulatory system, e.g., smaller systemic arteries or arterioles leading to the heart, brain, kidney or lungs. Thrombus and platelet aggregation do not normally form in normal healthy blood vessels. This is because the endothelium releases prostacyclin and nitric oxide, which prevent the formation of thrombi and inhibit platelet aggregation.

Atherosclerosis is a disease of the arteries in which fatty lesions called atheromatous plaques develop on the inside of arterial walls. These plaques are formed by deposition of minute crystals of cholesterol in the intima and smooth muscle of the vessel. The crystals grow larger over time and eventually coalesce to form larger crystals. In addition, the surrounding fibrous and smooth muscle tissues proliferate to form additional layers, which grow over time to form larger and larger plaques. The plaque and the cellular proliferate become so extensive in the arteries that eventually it leads to blockage of the blood flow in the vessel. Further, such extensive amounts of plaque are deposited into the arteries, so that eventually the arteries become stiff and unyielding and they lose their distensibility. In addition, calcium salts often precipitate with the cholesterol and other lipids, leading to calcification, which causes the arteries to form rigid tubes. Because of the degenerative areas in their walls, the arteriosclerotic arteries are easily ruptured. When an atherosclerotic artery ruptures, causing the surface thereof to become rough, the endothelium becomes damaged and cannot release the aforementioned protective mediators. Further, where plaque protrudes into the flowing blood, the roughness of the surface causes clots to develop, and eventually leads to the formation of a thrombus or an embolus.

More specifically, platelets adhere to a ruptured plaque via their glycoprotein receptors, and release a number of active substances such as adenosine diphosphate (ADP), thromboxane A2 (TXA2) and fibrinogen. These agents, among other agents, promote aggregation of platelets. In addition, through a series of reactions, a complex of substances called prothrombin activator is formed in response to the rupture of the blood vessel; the prothrombin activator catalyzes the conversion of prothrombin into thrombin. The thrombin converts fibrinogen into fibrous threads, enmeshing platelets, blood vessels and plasma to form a clot. Because of the occlusion of the blood vessels, blood flows slowly therethrough and forms clots, which can lead to the formation of a thrombus or an embolus.

To combat the adherence of platelets, and inhibit the clotting action, anti-platelet drugs have been administered to patients. While there are a number of such drugs, they can be broadly classified under platelet COX-1 inhibitors, Glycoprotein IIb/IIIa inhibitors and prostacyclin enhancers.

These anti-platelets, which include aspirin, Clopidogrel and dipyridamole, are currently being used to treat MI. Each of these is described below.

Low doses of aspirin have been shown to be of benefit for preventing or treating stroke and MI. As low a maintenance dose of 75 mg per day of aspirin has shown to be effective. Aspirin inhibits the COX enzyme in platelets, which, in turn, inhibits synthesis of TXA2. Aspirin also inhibits prostacyclin. In theory, these two actions should cancel each other, but the endothelium is able to produce more COX enzymes, while the platelets cannot. The endothelium also requires a higher dose of aspirin to inhibit its COX enzyme than that required by the platelets; thus a low dose of aspirin is effective.

However, many patients suffer from serious side effects from aspirin, the most significant being gastrointestinal ("GI") upset, irritation and bleeding. Also concurrent administration of other non-steroidal anti-inflammatory drugs ("NSAIDs") significantly increases the occurrences of these side effects. Aspirin also interacts with many other classes of drugs, either making them less effective or more toxic (anti-coagulants, methotrexate and the like).

Clopidogrel has been shown to be somewhat more effective than aspirin in some of the clinical trials. Clopidogrel has a more selective mechanism of action, as it inhibits the binding of the platelet aggregator ADP to its membrane receptors. Unlike aspirin, Clopidogrel does not inhibit COX enzymes. However, the incidence of GI side effects in many clinical trials with Clopidogrel showed that it exhibited the same GI toxicity profile as aspirin. Diarrhea and rashes are more common with Clopidogrel than aspirin. Other side effects include abdominal discomfort, nausea, vomiting, headache, dizziness and thrombocytopenia (abnormally low levels of platelets in the circulating blood).

Similar to aspirin, an increased bleeding is observed when NSAIDs are co-administered with Clopidogrel; and Clopidogrel prolongs the bleeding time of anti-coagulants.

Dipyridamole is used along with aspirin in the prevention of thromboembolism associated with prosthetic heart valves. Also it is used in the prevention of ischemic stroke and transient ischemic attacks, either alone or with aspirin. While the mode of action of Dipyridamole is unclear, it is thought to inhibit the adhesion of platelets to the damaged wall, increase the potency of prostacyclin (which reduces aggregation) and is responsible for other beneficial effects, including vasodilation. But again, dipyridamole has several adverse side effects associated therewith. For example, hepatic failure and elevated hepatic enzymes have been reported in association with dipyridamole administration. Moreover, its administration to patients with underlying coronary disease can aggravate chest pain.

SUMMARY OF THE INVENTION

There are a number of anti-platelet drugs in the market that are useful in the treatment of a number of vascular diseases such as MI or stroke. However all the drugs have potential side effects or other health complications.

The present invention is directed to anti-platelet drugs that are also nutritional and/or vitamin supplements that can prevent or treat vascular disease. These anti-platelet drugs are derived from natural amino acids. They virtually have no side effects; hence, they possess very high therapeutic index. More specifically, they are acetylated derivatives of the hydroxyl containing naturally occurring amino acids such as serine, carnitine, threonine, hydroxyproline, tyrosine, 5-hydroxylysine and the like or pharmaceutically acceptable salts thereof or they are dipeptides, tripeptides, tetrapeptides or pentapeptides or hexapeptides of the hydroxy containing amino acids in which at least one of the hydroxy groups in the peptide is acetylated or a mixture thereof. The present invention is also directed to a pharmaceutical and nutritional supplement composition comprising the acetylated ester of the naturally occurring amino acids and/or dipeptide, tripeptide, tetrapeptide or pentapeptide or hexapeptide, each having a hydroxy group on the side chain or pharmaceutically acceptable salts in association with a pharmaceutical and/or nutritional supplement carrier wherein at least one of the hydroxy groups on the side chain is acetylated.

The present invention is also directed to a method of reducing aggregation of platelets in the blood of a mammal which method comprises administering to said mammal in need of treatment an anti-platelet effective amount of an acetyl ester of a naturally occurring amino acid or a dipeptide, tripeptide, tetrapeptide or pentapeptide, or hexapeptide, each having at least one hydroxy group on the side chain thereof or a pharmaceutically or nutritionally acceptable salt thereof, wherein at least one of the hydroxy groups on the side chain of said amino acid or dipeptide, tripeptide, tetrapeptide, pentapeptide or hexapeptide is esterified with the acetyl group or mixture thereof.

The present invention is also directed to a method of treating or preventing diseases in a mammal resulting from or caused by platelet aggregation comprising administering to said mammal in need of treatment an anti-platelet effective amount of an acetyl ester of a naturally occurring amino acid or dipeptide, tripeptide, tetrapeptide or pentapeptide or mixture thereof, each amino acid, including the amino acids in the peptide having an hydroxy group on the side chain thereof or a pharmaceutically and/or nutritionally acceptable salt thereof, wherein at least one of the hydroxy groups of the side chain of said amino acid or dipeptide, tripeptide, tetrapeptide, pentapeptide or hexapeptide is esterified with the acetyl group.

DETAILED DESCRIPTION OF THE PRESENT INVENTION

Figure 1:
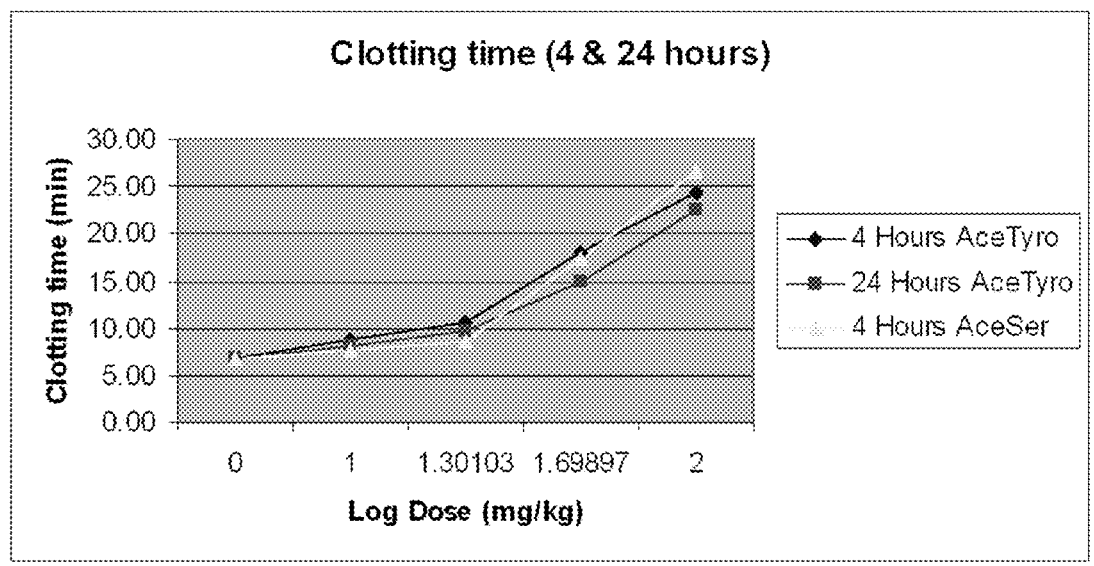
FIG. 1 graphically depicts the average clotting time in minutes in a rat against log of the dose administered thereto.

As defined herein, a peptide is an amino acid chain having 2 or more amino acid residues. The preferred peptides contain 1-5 peptide bonds, i.e., dipeptide, tripeptide, tetrapeptide, pentapeptide or hexapeptide.

The term "hydroxy containing naturally occurring amino acid" refers to an amino acid, which is available naturally, having a hydroxy group on the side chain.

It is to be understood that the term "hydroxy containing naturally occurring amino acid" does not mean that the hydroxy containing amino acid utilized in the present invention to make the acetylated product must be derived from a natural source. It only refers to the fact that it can be naturally found. However, although it can be naturally found, one of ordinary skill in the art may instead synthesize it. Thus, to that extent, the hydroxy containing naturally occurring amino acid can be synthesized. For example, L-serine is a naturally occurring amino acid. The L-serine used may be the L-serine which is isolated from a natural source or it can be synthesized; it makes no difference. The acetylated amino acid described in the present invention can be derived from either L-serine made chemically or naturally.

The term "acetylated hydroxyl containing naturally occurring amino acid" or synonym thereto refers to a naturally occurring amino acid, as defined herein, having one or more hydroxy group on the side chain wherein at least one of the hydroxy groups on the side chain is acetylated.

As indicated hereinabove, there has been a significant amount of research conducted to develop safe and effective anti-platelet drugs. While aspirin is inexpensive, it is associated with a number of side effects. Clopidogrel is a more expensive counterpart to aspirin, but it has not shown any less side effects. These drugs also do not work consistently in all patients who ingest them. For example, it has been reported that there are aspirin "responders" and aspirin "non-responders". In certain studies, it was noted that similar non-responders exist for Clopidogrel treatment as well. In some studies, it was reported that aspirin and Clopidogrel non-responders varied between 25% to as high as 40%. This is clearly an indication of lack of good treatment response among patients who subsequently have heart attacks and strokes.

A number of new drugs of different therapeutic modality have also been synthesized, such as Ticlopidine and the like. But, Ticlopidine can cause life threatening hematological adverse reactions including neotropenia/agranulocytosis, thrombotic thrombocytopenic purpura (TTP) and aplastic anemia. Thus, these drugs suffer from significant side effects, hence limiting their use in the treatment of various vascular diseases.

The present inventor has found that acetylated derivatives of naturally occurring amino acids or peptides of same, e.g., dipeptides, tripeptides, tetrapeptides and pentapeptides and hexapeptides containing OH groups, wherein at least one of the hydroxyl groups is acetylated, are surprisingly potent inhibitors of COX enzymes in the platelets, and hence act as superior anti-platelet drugs. Since they are simple acetylated amino acids or peptides, they can be classified as nutritional supplements, and therefore can be positioned in the market for immediate consumption by the public to improve their cardiovascular health. Thus, an aspect of the present invention is directed to acetylated naturally occurring amino acids having a hydroxy group on the side chain and to the pharmaceutically and nutritionally acceptable salts thereof, wherein the acetyl group is acetylated on the hydroxy group on the side chain. As described herein, the acetylated amino acids are prepared from the naturally occurring hydroxy containing amino acids in the L-configuration. Although there may be more than one hydroxy group present on the side chain, the preferred hydroxy containing amino acids have only one hydroxy group in the side chain. However, if the amino acid has more than one hydroxy group on the side chain, the present invention includes those compounds or pharmaceutically and nutritionally acceptable salts thereof wherein one or more (including all) of the hydroxy groups are acetylated. Examples of naturally occurring amino acids having a hydroxy group on the side chain include hydroxyproline, threonine, serine, tyrosine, 3'-iodotyrosine, 5'-iodotyrosine, 3'5'-di-iodotyrosine, α-methyl-m-tyrosine, metyrosine, 5-hydroxylysine, and the like. Carnitine is another example of an amino acid having an OH group in the side chain. It is preferred that the hydroxy containing amino acids used to prepare the acetylated amino acids are in the L-configuration at the carbon atom to which the amino and the carboxy groups are bonded. In addition, it is preferred that the carnitine is in the L-configuration. The hydroxy containing amino acids used to prepare the acetylated amino acids may contain other asymmetric carbons, which can exist in either the D or L configuration at each of the other asymmetric carbons. All such stereoisomers resulting therefrom are contemplated to be within the scope of the present invention.

Thus, in accordance with the present invention, in an embodiment of the present invention, the hydroxy group on the side chain of a naturally occurring amino acid is acetylated. If the amino acid contains more than one hydroxy group on the side chain, the present invention contemplates the product wherein at least one of the hydroxy groups on the side chain is acetylated. Thus, depending on the number of hydroxy groups present on the side chain, the present invention contemplates acetylated amino acids wherein all of the hydroxy groups on the side chain are acetylated, one less than all of the hydroxy groups on the side chain are acetylated, two less than all of the hydroxy groups on the side chain are acetylated, etc. all the way down to only one of the hydroxy groups on the side chain being acetylated. It is preferred that the amino acid has only one, two or three hydroxy groups on the side chain, and more preferably one or two hydroxy groups on the side chain, and most preferably only one hydroxy group on the side chain so that the preferred products of the present invention include mono-acetylated hydroxy containing amino acids. Examples of acetylated hydroxy containing amino acids include:

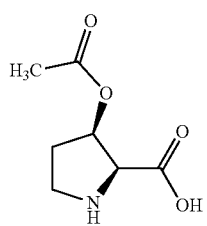

O-Acetyl-L-Hydroxyproline

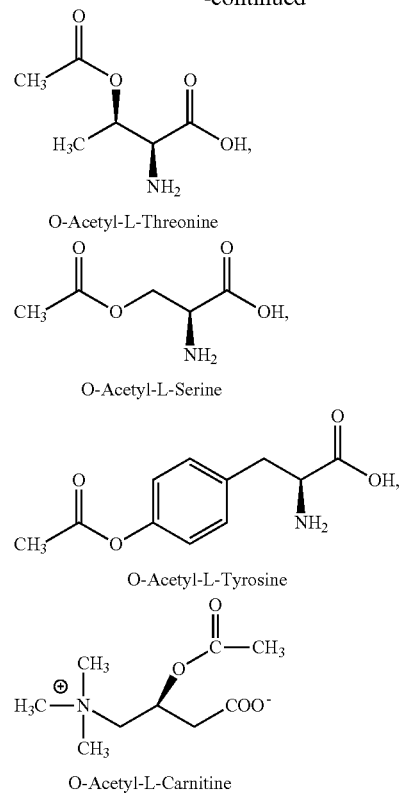

O-Acetyl-L-Threonine

O-Acetyl-L-Serine

O-Acetyl-L-Tyrosine

O-Acetyl-L-Carnitine as well as mono and di-acetylated homogentisic acid, 5-O-acetyl-L-lysine, O-acetyl-L-3',5'-diiodotyrosine, O-acetyl-3-L-iodotyrosine, O-acetyl-5'-iodotyrosine, alpha-methyl-m-o-acetyl tyrosine, O-acetyl metyrosine, and the like. The preferred acetylated amino acids are O-acetyl L-hydroxyproline, O-acetyl-L-threonine, O-acetyl-L-serine, and O-acetyl-L-tyrosine and O-acetyl-L-carnitine. As with the amino acids, the preferred O-acetylated amino acids have the L configuration at the asymmetric carbon atom that is alpha to the carboxy and amino groups of the acetylated amino acids, that is, the carbon atom to which the side chain is attached. Another preferred O-acetylated amino acid is O-acetyl-L-Carnitine, wherein the carbon atom to which the hydroxy side chain is attached is in the L-configuration.

The acetylated amino acids may contain more than one asymmetric carbon thereon and the various stereoisomers resulting therefrom are contemplated by the present invention. Nevertheless, it is still preferred that the carbon atom which is alpha to the amino group and the carboxy group and which is attached to the side chain containing the acetyl group is in the L configuration as it occurs in the nature.

Peptides with Anti-Platelet Activity:

The present invention further contemplates peptides, e.g., dipeptides tripeptides, tetrapeptides and pentapeptides, and hexapeptides derived from the naturally occurring amino acids wherein at least one of the hydroxy groups on the side chain of the amino acids in the peptide is acetylated. These peptides are prepared from the corresponding amino acids, but in an embodiment of the present invention only one of the amino acids used to prepare the peptides is required to have a hydroxy group, which is acetylated on the side chain. Thus, the dipeptide, tripeptide, tetrapeptide or pentapeptide may only have only one hydroxy group on the side chain, which is acetylated. Thus, when forming the peptides, only one of the amino acids may have a hydroxy group on the side chain, which is acetylated. For example, the peptide may have two or more hydroxy groups on the side chain, but only one is acetylated. In other embodiments, all of the hydroxy groups on the side chain are acetylated, one less than all of the hydroxy groups on the side chain are acetylated, two less than all of the hydroxy groups on the side chain are acetylated, etc, all the way down to one of the hydroxy groups on the side chain being acetylated.

In another embodiment, the present invention is directed to a mixture of two to six compounds selected from the group consisting of hydroxy containing naturally occurring amino acids and acetylated hydroxy containing naturally occurring amino acids or pharmaceutically acceptable salts of said compounds or a Zwitterion of said compounds, wherein at least one of the side groups of at least one of the amino acids is acetylated, while each of the remaining amino acids have at least one side group containing a hydroxy group. Such a mixture, of 2, 3, 4, 5, or 6 amino acids corresponds to the dipeptides, tripeptides, tetrapeptides, pentapeptides and hexapeptides, respectively, described hereinabove. Any of the amino acids having a hydroxy side group or any amino acid wherein a hydroxy group on the side chain is acetylated can be present in the mixture. Moreover the mixture can contain the acetylated amino acids and the hydroxy containing amino acid of the same amino acid, e.g., O-Acetyl Tyrosine and Tyrosine. The only criteria is that one of the hydroxy groups on the side chain must be acetylated. Furthermore the acetylated hydroxy containing naturally occurring amino acid is present in anti-platelet effective amounts, as defined herein. If more than one of the amino acid side chains is acetylated, then the total amount of acetylated amino acids is present in anti-platelet inhibiting amounts, as defined herein. Although Carnitine and O-Acetyl Carnitine may be present, it is preferred that O-Acetyl Carnitine is the only active ingredient (only acetylated hydroxyl containing naturally occurring amino acid) in the composition.

It is preferred that the amino acid residues in the peptide are naturally occurring amino acids. Moreover, it is preferred that the amino acid residues of the peptides are α or β amino acids, and if they have an asymmetric carbon on the carbon atom to which the side chain is attached, it is in the L-configuration. There may be other asymmetric carbons on the amino acid residues of the peptides, and the various stereoisomers resulting therefrom are contemplated by the present invention. The preferred amino acids from which the peptides are prepared are the hydroxy containing amino acids described hereinabove.

In a further embodiment, the present invention contemplates dipeptides derived from two, three, four, fix or six hydroxy containing amino acids, which may be the same, or different wherein at least one of the hydroxy groups on the side chain is acetylated. It is preferred that the dipeptides are derived from the basic 5-O-acetylated amino acids, such as Hydroxyproline, Serine, Threonine and Tyrosine, or from Carnitine. These will have the same or improved therapeutic and pharmaceutical and nutritional supplemental properties compared to their individual monomers. It is also preferred that at least two of and more preferably two, three, four, five or six or all of the hydroxy groups on the side chain are acetylated. In fact, from hydroxyproline, serine, threonine, tyrosine and carnitine the following 20 different combinations are possible, going from the amino end of the dipeptide to the carboxy end, wherein all of the dipeptides listed below are understood to be di-acetylated at their respective OH positions. (Nomenclature: Ser=Serine, Hyp=Hydroxyproline, Thr=Threonine, Car=Carnitine, and Tyr=Tyrosine): Di-O-acetyl-Ser-Ser, di-O-Acetyl-Ser-Thr, di-O-Acetyl-Thr-Ser, di-O-Acetyl-Ser-Hyp, di-O-Acetyl-Hyp-Ser, di-O-Acetyl-Thr-Thr, di-O-Acetyl-Thr-Tyr, di-O-Acetyl-Tyr-Thr, di-O-Acetyl-Thr-Hyp, di-O-Acetyl-Hyp-Thr, di-O-acetyl-Tyr-Tyr, di-O-Acetyl-Tyr-Hyp, di-O-Acetyl-Hyp-Tyr, di-O-acetyl-Hyp-Hyp, di-O-Acetyl-Ser-Tyr, di-O-Acetyl-Tyr-Ser, di-O-Acetyl-Car-Ser, di-O-Acetyl-Car-Hyp, di-O-Acetyl-Car-Thr, and di-O-Acetyl-Car-Tyr.

Thus the total dipeptide combination of the amino acid residues from Ser, Hyp, Thr, Car and Tyr are 20. In the above, the dipeptides are formed from the carboxy group of one amino acid and the amino group of a second amino acid. For example, for Serine-Threonine diacetylated dipeptide, L-Serine can be covalently bonded via its COOH group with the $NH_2$ group of the Threonine to form the (C=O)—NH amide bond. In another example, the $NH_2$ group of the L-Serine can be bonded to the COOH group of the L-Threonine to form NH—(C=O) amide bond.

Each of the above di-acetylated dipeptides is readily transformed in the body by a vast number of GI, liver and blood proteolytic enzymes to generate monomeric acetylated amino acids. For example, Di-acetylated Seryl Serine, are hydrolyzed in vivo to form 2 molecules of Acetyl-L-Serine, which would exert its anti-platelet activity in the blood.

The acetyl ester of a naturally occurring amino acid or dipeptide, wherein at least one of the hydroxy side groups of the amino acid residue is acetylated, or pharmaceutically acceptable salts of either or combination thereof are most preferred.

Thus the di-acetylated dipeptides shown above will not only be active intact, they will also generate corresponding active metabolites, which are monomeric acetylated amino acids, which are also efficacious.

For example, by subjecting O,O-Diacetyl-L-Threonyl-L-hydrodroxyproline to proteolytic enzymes found in either the GI, liver or blood, O-Acetyl-L-HydroxyProline and O-Acetyl-L-Threonine are formed. The reaction is depicted as follows:

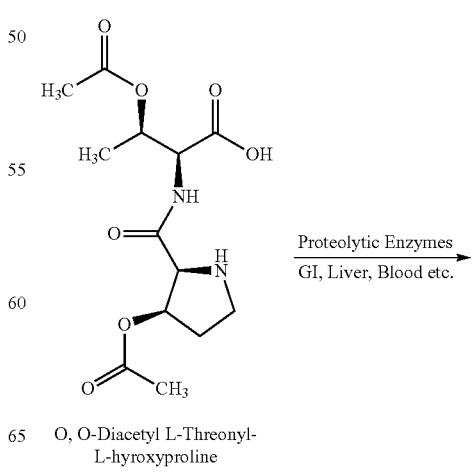

O, O-Diacetyl L-Threonyl-L-hyroxyproline

Proteolytic Enzymes
GI, Liver, Blood etc.

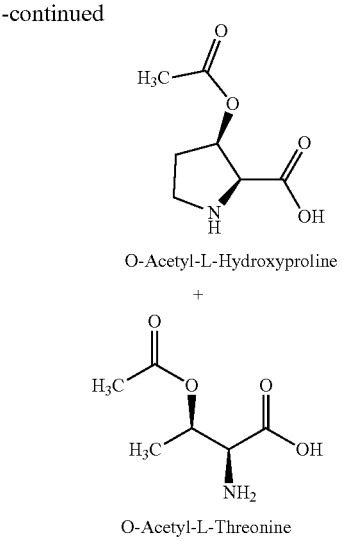

O-Acetyl-L-Hydroxyproline

+

O-Acetyl-L-Threonine

As another example, O-Acetyl-L-Serine and O-Acetyl-L-Tyrosine are released in the mammalian system by subjecting O,O-Diacetyl-L-Tyrosyl-L-Serine to proteolytic enzymes found in either the GI, liver and blood. The reaction is depicted as follows:

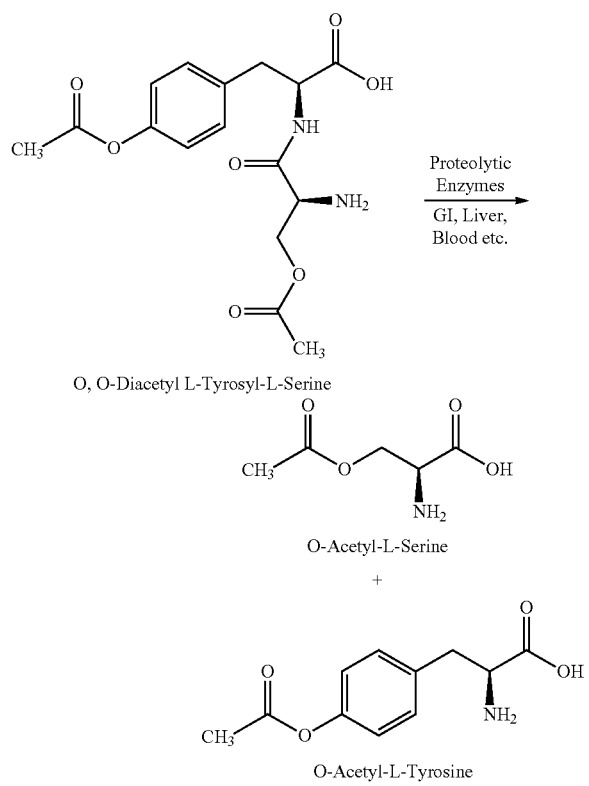

Furthermore, these monomeric acetylated amino acids as well as the diacetyled amino acids as well as the other embodiments of the present invention, do not exhibit the adverse side effects of the NSAIDs, described hereinabove.

Moreover, the tripeptides, tetrapeptides, pentapeptides and hexapeptides will not only be active intact, but will also generate active metabolities, which are small peptides units and/or one monomeric acetylated amino acids, which are also efficacious. Moreover, none of these products exhibit the adverse side effects of the NSAIDS.

The inventor further contemplates that polypeptides derived from the basic 5 O-acetylated amino acids, such as Hydroxyproline, Serine, Threonine, Carnitine and Tyrosine will have the same or improved therapeutic and pharmaceutical and nutritional supplemental property compared to their individual monomers. However, the number of amino acids in any such polypeptide can contain from 2-6 residues, with at least one amino acid in that 2-6 member polypeptide shall have an acetylated group. In case of simple dipeptides, all of the dipeptides are preferably mono- or di-acetylated at their respective OH positions on the side chains of each of the amino acid residues in the dipeptide.

However; the present invention is not limited to dipeptides as described above. The number of amino acids can vary from 2 to 6 peptides attached via CO—NH bond between each of the amino acids, and the 2-6 member amino acids shall contain at least one acetylated hydroxy containing naturally occurring amino acid (such as O-Acetyl-Serine, O-Acetyl-Threonine, O-Acetyl Hydroxy Lysine, O-Acetyl Tyrosine, O-Acetyl Carnitine or O-Acetyl HydroxyProline and the like) and the remaining amino acids on the peptide are hydroxy containing naturally occurring amino acids. The present invention also contemplates that there could be more than one acetylated amino acid in the 2-6 polypeptide molecules or in the mixture of the amino acids. The following are typical examples of the polypeptide which are non-limiting:

O-Acetyl Ser-Thr-O-Acetyl-Hyp-Tyr
O-Acetyl Ser-Ser-O-Acetyl Car

The present invention also contemplates mixtures of one or more acetylated hydroxy containing amino acids as described hereinabove, and/or, or one or more peptides of hydroxy containing amino acids in which at least one of the hydroxy groups on the side are acetylated, as defined herein or a combination of one or more acetylated hydroxy containing amino acids and/or one or more peptides (e.g., dipeptide, tripeptide, tetrapeptide, pentapeptides or hexapeptides) in which at least one of the hydroxy groups on the side chain is acetylated in which at least one of the hydroxy side chain of the dipeptide is acetylated.

The present invention also contemplates pharmaceutically and nutritionally acceptable salts of the O-acetylated hydroxy containing amino acids and peptides. These include acidic and basic salts thereof, especially since the acetylated amino acids of the present invention except for carnitine and other carnitine containing peptides, contain an acid (carboxyl) and basic (amino) functionalities. Carnitine is a zwitterion, containing a positively changed ammonium group and a negatively charge COO⁻ group. It, however, can form salts just like the other amino acids described hereinbelow.

Pharmaceutically and nutritionally acceptable salts include the acid addition salts which are inorganic or organic acids, e.g. nitrate, hydrochloride, hydrobromide, sulfate, bisulfate, perchloride, phosphate, acetate, trifluoroacetate, formate, propionate, gluconate, lactate, oxalate, malate, maleate, tartrate, citrate, benzoate, cinnamate, fumarate, methanesulphonate, salicylate and the like. Suitable basic salts are formed from inorganic or organic bases which form non-toxic salts and include, e.g. alkali or alkaline-earth metals, especially sodium, potassium, calcium, magnesium, aluminum, zinc and ammonium salts.

A pharmaceutically and nutritionally acceptable salt of a compound of the present invention may be readily prepared by mixing together solutions of an acetylated hydroxy containing naturally occurring amino acid and the desired acid or base, as appropriate. Alternatively, the acid salt may be prepared under the reaction conditions of the acetylation reaction or by converting the amino acid or peptide to the acid additive salt before the acetylation reaction. The salt may precipitate from solution and be collected by filtration or be recovered by evaporation of the solvent. Salts may also be prepared by ion exchange, such as by equilibrating a solution of a compound of the present invention with an appropriate ion exchange resin. Ion exchange may also be used to convert one salt form of the acetylated amino acid, such as a salt with an acid or base that is not pharmaceutically acceptable to another salt form. These methods are generally well known in the art.

The compounds of the present invention can be prepared by art-recognized techniques or are commercially available. For example O-Acetyl-Serine and O-Acetyl-Tyrosine are commercially available. However, if not purchased, the acetylated amino acids of the present invention are prepared by acetylating with acetic acid the naturally occurring essential and non-essential amino acids and/or peptides having a hydroxy group on the side chain under conditions effective to form the O-acetyl derivatives. For example O-Acetyl-Tyrosine is prepared by reacting tyrosine with acetyl chloride in the presence of trifluoroacetic acid. Examples of the preparation of O-Acetyl amino acids are described in 1) Specific O-Acylation of Hydroxylamino Acids in the Presence of Free Amino Acids, Previero, A., Barry, L.-G., Coletti-Previero, M.-A., *Biochimica et Biophysica Acta,* 1972, 263(1), pages 7-13; 2) Synthesis of Tryosyltyrosyltyrosine and Tyrosyltyrosyltyrosyltyrosine, Barkdoll, A. E., Ross, W. F., *Journal of the American Chemical Society,* 1944, 66, 951-956; 3) The Investigations of Amino Acid Reactions by Methods of Non-Aqueous Titrimetry, Sakami, W., Toennies, G., *Journal of Biological Chemistry,* 1942, 144, 203-216; and 4) Chong Heng, H., Kimura R., Bawarshi-Nassa, R., Hussain, A., *Journal of Pharmaceutical Science,* 1985, 74(12), 1298-1301, the contents all of which are incorporated by reference. It is preferred that the reactions are conducted in an inert solvent or mixtures of inert solvents, that is, the solvent(s) is (are) non-reactive under acetylation reaction conditions. Examples of such solvents include ethers, such as ethyl ether, THF, dioxane, chloroform, methylene chloride and the like. It is also preferred that the reaction is conducted at effective temperatures, e.g., ranging from the room temperature up to the boiling point of the solvent. The reaction can be effected with the amino acid in its zwitterionic form or in its salt form.

The dipeptides, tripeptides, tetrapeptides, pentapeptides and hexapeptides are prepared by peptide syntheses known in the art. If all of the hydroxy groups on the side chain are acetylated, a peptide containing the hydroxy containing amino acids can be prepared followed by acetylation thereof under acetylating conditions known in the art. If not all of the hydroxy groups in the peptide are acetylated, it is preferred that the acetylated hydroxy containing naturally occurring amino acids be prepared first and then the products thereof are coupled with the amino acids or peptides in which the hydroxy groups are not acetylated under peptide forming conditions known in the art, e.g., by solution chemistry or solid phase peptide synthesis.

If substituents on the naturally occurring amino acids or peptides each having a hydroxy group on the side chain are themselves reactive under the reaction conditions, then these substitients can themselves be protected utilizing protecting groups known in the art utilizing known chemical techniques. A variety of protecting groups known in the art may be employed. Examples of such protecting groups can be found in the book entitled "Protective Groups in Organic Synthesis", by T. W. Greene, John Wiley and Sons, NY, N.Y. 1981, the contents of which are incorporated by reference. As one skilled in the art is well aware, the protecting groups, if any, are placed on the naturally occurring amino acids with a hydroxy side chain or the peptide having hydroxy groups on the side chain thereon prior to the acetylation reaction and are removed after the acetylation reaction by the methods described in the aforementioned book by Greene utilizing techniques known in the art.

The acetylated naturally occurring amino acids and peptides of the present invention may be further purified by techniques known by one of ordinary skill in the art, such as by chromatography, e.g., HPLC, column chromatography, preparative thin layer chromatography, gas chromatography, and the like; crystallization techniques and the like. It is preferred that the acetylated naturally occurring amino acids and dipeptides utilized in the pharmaceutical composition and in the nutritional composition, and in the methods of the present invention are enantiomerically pure, i.e., is substantially free of the corresponding D isomer at the carbon atom which is alpha to the amino group and the carboxy group of the amino acid, except for carnitine wherein enantiomerically pure refers to the acetylated carnitine compounds which is substantially free of the corresponding D isomers at the carbon atom to which is attached the acetyl ester. Preferably, the acetylated amino acids or peptides of the present invention contain less than about 50% D isomer at the aforementioned carbon atoms and more preferably less than about 40% D isomer at the aforementioned carbon atoms, and even more preferably less than about 25% D isomer at the aforementioned carbon atoms, and especially more preferably less than about 10% D isomer at the aforementioned carbon atoms and most preferably less than about 5% D isomer at the aforementioned carbon atoms. In addition, the acetylated amino acids and/or peptides of the present invention are substantially pure, i.e., substantially free of impurities, including the corresponding D isomers at the asymmetric carbons referred to hereinabove in this paragraph. More specifically, it is preferred that the acetylated naturally occurring amino acid or peptide is at least 50% pure and more preferably at least about 60% pure and even more preferably at least about 75% pure and especially more preferably at least about 90% pure and even more especially preferably at least about 95% pure and especially most preferably at least about 98% pure.

The acetylated hydroxy containing amino acids and peptides and/or mixtures thereof of the present invention are useful for reducing platelet aggregation. The acetylated naturally occurring amino acids and peptides of the present invention are present in these compositions in platelet inhibiting effective amounts as defined herein.

In addition, the acetylated hydroxy containing amino acids and peptides as defined herein, may be present in the pharmaceutical and/or nutritional composition with other acetylated hydroxy containing naturally occurring amino acids or peptides or with other active drugs or other nutritional supplements. If other nutritional supplements or drugs are present in the pharmaceutical and or nutritional compositions, it is preferred that the other drugs/nutritional supplements possess anti-platelet activity. Examples include aspirin, clopidogrel, dipyrimidamole, Ticlopidine and the like. If a second drug or a nutritional supplement, especially an anti-platelet drug, is present in the pharmaceutical composition, it is preferred that the molar ratio of the total of the acetylated hydroxy containing amino acid of the present invention or peptide of the present invention to the second drug or nutritional supplement, including another anti-platelet drug or nutritional supplement, ranges from about $10^{-6}$ to $10^6$ and more preferably from about 1:1 to about 100:1. Preferably, the ratio of the acetylated hydroxy containing amino acid or dipeptide of the present invention to any additional drug, or nutritional supplement is greater than 1:1.

Another embodiment of the present invention is a pharmaceutical composition comprising an anti-platelet inhibiting effective amount of acetylated hydroxy containing naturally occurring amino acids or peptides of the present invention in association with a pharmaceutically acceptable carrier therefor. The pharmaceutical composition may contain one such acetylated amino acid and/or peptide as defined herein, or a mixture of more than one such acetylated hydroxy containing naturally occurring amino acids or peptide. Although in one embodiment, the pharmaceutical composition may contain O-Acetylated Carnitine, which may be present as the only amino acid or in combination with other acetylated hydroxyl containing naturally occurring amino acid or peptide comprised of same. It is preferred that it is not the only active ingredient present or if it is present with other acetylated hydroxy containing naturally occurring amino acids or peptides, the other amino acids or peptides are present in platelet inhibiting effective amounts. In another embodiment, the pharmaceutical composition excludes O-Acetylated Carnitine.

Another embodiment of the present invention is a nutritional composition comprising a nutritionally effective amount of the acetylated amino acid or peptide of the present invention in association with a nutritionally acceptable carrier therefor. The nutritional composition may contain one acetylated amino acid and/or peptide as described herein or a combination thereof and/or a hydroxy containing naturally occurring amino acid or peptide. In one embodiment, the nutritional composition may contain or O-Acetylated Carnitine, especially if it is not the only active ingredient present or if it is present with other acetylated hydroxy containing naturally occurring amino acids or peptides and the other amino acids or peptides are present in platelet inhibiting effective amounts. In another embodiment the nutritional composition excludes O-Acetyl Carnitine.

The compounds of the present invention are prepared into pharmaceutical and or nutritional compositions by techniques known to one of ordinary skill in the art. The compounds of the present invention are administered to patients, e.g., mammals, in therapeutic or prophylactic effective amounts, i.e., in amounts effective to inhibit platelet aggregation. The compounds of the present invention are preferably administered to mammals in amounts ranging from 0.0001 to 1000 mg/kg of mammalian body weight.

Nevertheless, the physician will determine the dosage of the acetylated amino acids or peptide which will be most suitable; and it may vary depending upon the form of administration and the particular compound chosen, and furthermore, it may vary depending upon various other factors, including but not limited to, the patient under treatment, the age of the patient, the severity of the condition being treated and the like. He will generally wish to initiate treatment with small dosages in amounts substantially less than the optimum dose of the acetylated amino acid or peptide of the present invention and increase the dosage by small increments until the optimum effect under the circumstances is reached.

The dosage regimen, moreover, may be adjusted by the physician to provide the optimum therapeutic or prophylactic response. For example, several divided doses may be administered daily or the dose may be proportionally reduced as indicated by the exigencies of the situation.

Since sufficient information regarding the usefulness of these O-acetylated amino acids and peptides as nutritional supplement are provided herein, the patient who is well read, familiar with the use of anti-platelet drugs and nutritional supplements in the prevention and treatment of cardiovascular diseases can self diagnose and self administer these O-acetylated amino acids as nutritional supplements without obtaining any counseling or prescription from a physician. The patient may simply purchase these O-acetylated amino acids or peptides over the counter worldwide from any of the retail pharmacy, grocery outlets, or via internet shops, and through various distribution centers catering to OTC drugs and supplements, thus avoiding the high cost of medical care.

The acetylated amino acids and/or peptides described herein may be administered as a drug or as a nutritional supplement in a convenient manner, such as by oral, intravenous, intramuscular or subcutaneous routes, rectally, buccally, or transdermally.

The acetylated amino acids or peptides of the present invention may be orally administered, for example, with an inert diluent or with an assimilable edible carrier, or it may be enclosed in hard or soft shell gelatin capsules, or it may be compressed into tablets, or it may be incorporated directly into ingested food, such as a cookie, cake, edible chocolate bar and the like; aqueous beverages, such as water, milk, tea, coffee, soda, lemonade, juice, and the like. Alternatively, they can be administered as a liquid, and may be suspended therein or made in solution in the liquid, examples of which include, water, beverage, juice, soup and the like. For oral therapeutic or prophylactic administration, the acetylated amino acid or peptide may be incorporated with excipients and used in the form of ingestible tablets, buccal tablets, troches, capsules, elixirs, suspensions, syrups, wafers, and the like. It is preferred that the acetylated amino acids and peptides be present in unit dosage forms. Such compositions and preparations should contain at least 1% of the acetylated amino acid or peptide. The percentage of the compositions and preparations may, of course, be varied and may conveniently contain between about 5 to about 80% by weight of the acetylated amino acid or peptide. The amount of the acetylated amino acid or peptide used in such therapeutic compositions is such that a suitable dosage will be obtained. Preferred compositions or preparations according to the present invention contain between about 25 mg to about 2000 mg of acetylated amino acid and approximately half as much of the acetylated dipeptide of the present invention if the dipeptide is comprised of amino acids which have only one hydroxy group on the side chain, and if both hydroxy groups are acetylated or approximately the same amount of only one of the hydroxy groups therein is acetylated, and approximately one third as much if a tripeptide is comprised of three amino acids, each having one hydroxy group on the side chain and all three hydroxy groups are acetylated, etc. Regardless of the size of the peptides, if only one of the hydroxy groups on the side chain is acetylated, the preferred composition will contain about 25 mg to about 2000 mg thereof; if two of the hydroxy groups of the side chain of the amino acid are acetylated, then the preferred amount will be about half as much; if three of the hydroxy groups of the side chain of the amino acid are acetylated, then the preferred amount will be about a third as much, etc.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier.

Various other materials may be present as coatings or otherwise modify the physical form of the pharmaceutical or nutritional composition of the present invention. For instance, tablets, pills, or capsules may be coated with shellac, sugar or both. A syrup or elixir may contain the active compound, i.e., the acetylated amino acid or peptide, sucrose as a sweetening agent, methyl and propylparabens as preservative, a dye and flavoring such as cherry or orange flavor. Of course, any material used in preparing any dosage unit form should be pharmaceutically pure and substantially non-toxic in the amounts employed. In addition, the acetylated amino acid or dipeptide may be incorporated into sustained-release preparations and formulations. For example, sustained release dosage forms are contemplated wherein the acetylated amino acid or peptide is bound to an ion exchange resin which, optionally, can be coated with a diffusion barrier coating to modify the release properties of the resin or wherein the active ingredient, i.e., the acetylated amino acid, is associated with a sustained release polymer known in the art, such as hydroxypropylmethylcellulose and the like.

The acetylated amino acids and peptides may be administered in the form of a solution or suspension filled soft or hard gelatin capsule. Such capsules are generally made of gelatin, glycerin, water and sorbitol. Hard capsules are distinguished from soft capsules by containing less water and thus having a correspondingly stronger shell. Additional excipients suitable for use in such capsules include propylene glycol, ethanol, water, glycerol and edible oils.

The active compound may also be administered parenterally for example, intravenously, intra-arterially, intraperitoneally, intrathecally, intraventricularly, intraurethrally, intrastemally, intracranially, intramuscularly, or subcutaneously. Such administration may be as a single bolus injection or as a short or long duration infusion. It is especially advantageous to formulate parental compositions in dosage unit form for ease of administration and uniformity of dosage. Dispersions can also be prepared in glycerol, liquid polyethylene glycols, e.g., PEG 100, PEG 200, PEG 300, PEG 400, and the like, and mixtures thereof and in oils. Under ordinary conditions of storage and use, these preparations contain a preservative to prevent the growth of microorganisms.

The pharmaceutical and nutritional forms suitable for injectable use include sterile aqueous solutions (where water soluble) or dispersions and sterile powders for the extemporaneous preparation of sterile injectable solutions or dispersions. In all cases, the form is usually sterile and must be fluid to the extent that syringability exists. It must be stable under the conditions of manufacture and storage and usually must be preserved against the contaminating action of microorganisms such as bacteria and fungi. The carrier can be a solvent or dispersion medium containing, for example, water, ethanol, polyol (for example, glycerol, propylene glycol, and one or more liquid polyethylene glycols, e.g., as disclosed herein and the like), suitable mixtures thereof, and vegetable oils. For such parenteral administration, the compounds are preferably formulated as a sterile solution in water or another suitable solvent or mixture of solvents. The solution may contain other substances, such as salts, particularly sodium chloride, and sugars, particularly glucose or mannitol, to make the solution isotonic with blood, buffering agents, such as acetic, citric and phosphoric acids and their sodium salts, such that the pH of the solution is preferably between 3 and 9; and a preservative. The preparation of suitable parenteral formulations under sterile conditions is readily accomplished by standard pharmaceutical techniques well known to those skilled in the art. The prevention of the action of microorganisms can be brought about by various antibacterial and antifungal agents, for example, parabens, chlorobutanol, phenol, sorbic acid, thimerosal, and the like.

In many cases, it will be preferable to include isotonic agents, for example, sugars or sodium chloride in these sterile aqueous solutions. Prolonged absorption of the injectable compositions can be brought about by the use in the compositions of agents delaying absorption, for example, aluminum monostearate and gelatin.

Sterile injectable solutions are prepared by incorporating the acetylated amino acids or peptides in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders, the above solutions are vacuum dried or freeze-dried, as necessary.

Alternatively, the acetylated hydroxy containing naturally occurring amino acids or peptides can be administered by the vaginal or rectal route in the form of the suppository or pessary. The compounds of the present invention may also be administered dermally or transdermally, for example, by the use of a skin patch. These compositions are prepared by standard pharmaceutical and/or nutritional supplement techniques well known to those skilled in the art.

The acetylated amino acids and peptides can also be applied topically, in the form of a gel, hydrogel, lotion, solution, cream, ointment or dusting powder. Suitable ointments may contain the compounds of the present invention suspended or dissolved in, for example, a mixture with one or more of the following: mineral oil, liquid petrolatum, white petrolatum, propylene glycol, polyoxyethylene, polyoxypropylene, emulsifying wax and water. Suitable lotions or cream may contain the acetylated hydroxy containing amino acids or dipeptides of the present invention suspended or dissolved in, for example, a mixture of one or more of the following: mineral oil, sorbitan monostearate, polysorbate 60, cetyl esters, wax, cetyl alcohol, 2-octyldodecanol, benzyl alcohol, water and the like.

The active ingredient can also be administered buccally by preparing a suitable formulation of the compounds of the present invention and utilizing procedures well known to those skilled in the art. These formulations are prepared with suitable non-toxic pharmaceutically and nutritionally acceptable ingredients. These ingredients are known to those skilled in the preparation of buccal dosage forms. Some of these ingredients can be found in Remington's Pharmaceutical Sciences, $17^{th}$ edition, 1985, a standard reference in the field. The choice of suitable carriers is highly dependent upon the exact nature of the buccal dosage form desired, e.g., tablets, lozenges, gels, patches and the like. All of these buccal dosage forms are contemplated to be within the scope of the present pharmaceutical and/or nutritional supplement invention and they are formulated in a conventional manner. Preferably, an effective amount of acetylated amino acid in the buccal form ranges from about 0.15 mg/Kg to 200 mg/Kg of body weight of the mammal, while the effective amount of the acetylated dipeptide in the buccal form is about one half of that amount an hydroxy group on each of the amino acids of the dipeptide is acetylated.

For example, the buccal dosage form comprises the acetylated amino acid or dipeptide in platelet inhibiting effective amounts, as defined herein in association with a pharmaceutically and nutritionally acceptable polymer carrier, preferably a biodegradable polymer that adheres to the wet surface of the buccal mucosa and which is biodegradable and which is described in more detail hereinbelow. In one embodiment, the buccal dosage form comprises the acetylated amino acid or dipeptide in effective amounts and the polymer. However, other excipients may optionally be present, e.g., binders, disintergrants, lubricants, diluents, flavorings, colorings, and like.

Ideally, the carrier comprises a polymer having sufficient tack to ensure that the dosage unit adheres to the buccal mucosa for the necessary time period, i.e., the time period during which the acetylated amino acids or dipeptides of the present invention are to be delivered to the buccal mucosa. Additionally, it is preferred that the polymeric carrier is gradually bioerodible, i.e., the polymer hydrolyzes at a predetermined rate upon contact with moisture. The polymeric carrier is preferably sticky when moist, but not when dry, for convenience in handling. Generally, it is preferred that the average molecular weight of the polymer ranges from about 4,000 to about 1,000,000 daltons. One of ordinary skill in the art will appreciate that the higher the molecular weight of the polymer the slower the erosion time.

Any polymeric carrier can be used that is pharmaceutically acceptable, provided both a suitable degree of adhesion and the desired drug release profile are obtained and provided it is compatible with the agents to be administered and any other components that may be present in the buccal dosage unit. Generally, the polymeric carriers comprise hydrophilic (water-soluble and water swellable) polymers that adhere to the wet surface of buccal mucosa. Examples of polymeric carriers useful herein include acrylic acid polymers and copolymers, e.g., those known as "carbomers" (Carbopol™ which may be obtained from GAF); vinyl polymers and copolymers; polyvinyl pyrrolidone, dextran, guar gum, pectins, starches; and cellulose polymers, such as hydroxypropylmethylcellulose (e.g., Methocel) obtainable from Dow Chemical Company, hydroxypropylcellulose (e.g., Klucel™; which may also be obtained from Dow), hydroxpropylcellulose ethers (see, e.g., U.S. Pat. No. 4,704,285 to Alderman), hydroxyethyl cellulose, sodium carboxymethyl cellulose, methyl cellulose, ethyl cellulose, cellulose acetate phthalate, cellulose acetate butyrate, and the like. The carrier may also comprise two or more suitable polymers in combination, for example, a carbomer combined in approximately 1:5 to 5:1 ratio, by weight, with a polyethylene oxide.

The dosage unit of the pharmaceutical and/or nutritional supplement composition of the present invention may contain only the acetylated amino acid of the present invention or peptide or any combination or mixture thereof and the polymeric carrier. However, it may be desirable in some cases to include one or more additional components. For example, a lubricant may be included to facilitate the process of manufacturing the dosage units; lubricants may also optimize erosion rate and drug flux. If a lubricant is present, it will be present on the order of about 0.01 wt. % to about 2 wt. %, preferably about 0.01 wt. % to about 0.5 wt, %, of the dosage unit. Suitable lubricants include, but are not limited to, magnesium stearate, calcium stearate, stearic acid, sodium stearylfumarate, talc, hydrogenated vegetable oils and polyethylene glycol. As will be appreciated by those skilled in the art, however, modulating the particle size of the components in the dosage unit and/or the density of the unit can provide a similar effect—i.e., improved manufacturability and optimization of erosion rate and drug flux—without addition of a lubricant.

Other components may also optionally be incorporated into the dosage unit. Such additional optional components include for example, one or more disintegrants, diluents, binders, enhancers, or the like. Examples of disintegrants that may be used include, but are not limited to, crosslinked polyvinylpyrrolidones, such as crospovidone (e.g., Polyplasdone® XL, which may be obtained from GAF), cross-linked carboxylic methylcelluloses, such as croscanmelose (e.g., Ac-di-sol®, which may be obtained from FMC), alginic acid, and sodium carboxymethyl starches (e.g., Explotab®, which may be obtained from Edward Medell Co., Inc.), agar, bentonite and alginic acid. Suitable diluents are those which are generally useful in pharmaceutical formulations prepared using compression techniques, e.g., dicalcium phosphate dihydrate (e.g., Di-Tab®, which may be obtained from Stauffer), sugars that have been processed by cocrystallization with dextrin (e.g., co-crystallized sucrose and dextrin such as Di-Pak®, which may be obtained from Amstar), calcium phosphate, cellulose, kaolin, mannitol, sodium chloride, dry starch, powdered sugar and the like.

Binders, if used, are those that enhance adhesion. It is preferred that binders are present. Examples of such binders include, but are not limited to, starch, gelatin and sugars such as sucrose, dextrose, molasses and lactose.

Permeation enhancers may also be present in the dosage unit form in order to increase the rate at which the active agents pass through the buccal mucosa. Examples of permeation enhancers include, but are not limited to, dimethylsulfoxide ("DMSO"), dimethyl formamide ("DMF"), N.N-dimethylacetamide ("DMA"), decylmethylsulfoxide ("$C_{10}$MSO"), polyethylene glycol monolaurate ("PEGML"), glycerol monolaurate, lecithin, the 1-substituted azacycloheptan-2-ones, particularly 1-n-dodecylcyclazacycloheptan-2-one (available under the trademark Azone®. from Nelson Research & Development Co., Irvine, Calif.), lower alkanols (e.g., ethanol), SEPA® (available from Macrochem Co., Lexington, Mass.), cholic acid, taurocholic acid, bile salt type enhancers, and surfactants such as Tergitol®, Nonoxynol-9® and Tween-80®.

Flavoring may be optionally included in the pharmaceutical and/or nutritional supplement composition. Any suitable flavoring may be used, e.g., mannitol, lactose or artificial sweeteners such as aspartame. Coloring agents may be added, although again, such agents are not required. Examples of coloring agents include any of the water-soluble FD&C dyes, mixtures of the same, or their corresponding lakes.

In general, the preferred dosage unit of the invention is compositionally a substantially homogeneous, substantially uniform formulation. By "substantially uniform" is meant that the dosage unit is not coated, and does not contain a plurality of layers or other types of discrete segments. Rather, the substance of the dosage unit is similar throughout, so that the unit is essentially "monolithic" in nature.

The dosage units may be in the form of tablets made by either conventional compression or molding methods. See e.g., Remington's Pharmaceutical Sciences, $18^{th}$ edition (Easton, Pa.: Mack Publishing Co., 1990). Preferably, the dosage units are prepared by mixing the components together and compressing the mixture into tablet form. As will be appreciated by those skilled in the art, the erosion rate of the dosage unit, and thus the rate of drug delivery, is controlled by three factors: the pressure used to make the tablets, and thus the tablet's density; the carrier selected, as alluded to above; and the carrier-to-drug ratio. Pressure, carrier and carrier-todrug ratio may thus be varied to obtain shorter or longer-lived dosage units.

The dosage units may have any of the conventional shapes, for example, lozenges, disks, wafers, tablets or the like.

As used herein, "pharmaceutically acceptable carrier" and/ or "nutritionally acceptable carrier" includes any and all solvents, dispersion media, coatings, antibacterial and antifungal agents, isotonic and absorption delaying agents for pharmaceutical active substances or in nutritional use, which are well known in the art. Except insofar as any conventional media or agent is incompatible with the active ingredient, their use in the pharmaceutical and/or nutritional compositions is contemplated. Supplementary active ingredients can also be incorporated into the compositions.

Dosage unit form as used herein refers to physically discrete units suited as unitary dosages for the subjects to be treated; each unit containing a predetermined quantity of active material calculated to produce the desired therapeutic or prophylactic effect in association with the required pharmaceutical carrier.

The acetylated hydroxy containing naturally occurring amino acid or dipeptide of the present invention is compounded for convenient and effective administration in effective amounts with a suitable pharmaceutically and or nutritionally acceptable carrier in dosage unit form as hereinbefore described. For purposes herein, the pharmaceutically effective amount, the anti-platelet inhibiting effective amount and the nutritionally effective amount or synonyms thereto are the same and are being used interchangeably. A unit dosage, for example, contains the principal active compound in amounts ranging from about 10 mg, or as low as 1 mg (for small animals) to about 2000 mg. If placed in solution, the concentration of the compounds of the acetylated hydroxy containing naturally occurring amino acid preferably ranges from about 0.1 mg/mL to about 500 mg/mL. In the case of buccal administration, the acetylated hydroxy containing amino acid in the buccal unit dosage form is present in an amount preferably ranging from about 1 to about 500 mg. In any of the nutritional or pharmaceutical compositions of the present invention, the peptides described herein contain at least one hydroxy group on the peptide, which is acetylated. If one of the hydroxy groups is acetylated then the amounts of the peptides are the same as that of the hydroxy containing amino acids, described hereinabove. If one of the hydroxy groups of one of the hydroxy containing amino acids is acetylated, while none of the hydroxy groups on the other amino acid is acetylated, then the amounts of the peptide is as the same as that of the hydroxy containing amino acids, described hereinabove. On the other hand, if at least one of the hydroxy groups of each of the amino acids in the peptide is acetylated, then the amount of peptide utilized is about one divided by the number of acetyl groups on the side chain relative to a mono-acetylated amino acid. For example, if a dipeptide has two of the hydroxy groups on the side chain acetylated, then the amount of dipeptide utilized is about one half of that of the acetylated hydroxy containing amino acids.

The peptides can also be formulated into pharmaceutical compositions using the procedures described herein. The various formulations described hereinabove with respect to the O-Acetyl L-Tyrosine, O-Acetyl-HydroxyProline, O-Acetyl-Threonine and O-Acetyl-L-Serine are also applicable to the aforementioned peptides. However, when administered, since each peptide contains 2-6 amino acid residues, depending on the size, and number of the side hydroxy group on each amino acid residue being acetylated, the peptides generate a mixture of O-acetylated amino acids, whereby at least one of the hydroxy groups on each amino acid of the dipeptide is acetylated; thus the therapeutic and prophylactic effective amounts are about one/# of amino acid residues having an acetylated hydroxy group relative to a mono acetylated amino acid.

The acetylated peptides contemplated by the present invention are prepared by art-recognized techniques. For example, two O-Acetyl amino acids described herein are reacted with each under peptide coupling reaction conditions to form a dipeptide.

As used herein the term "patient" or "subject" refers to a warm blooded animal, and preferably mammals, such as, for example, cats, dogs, horses, cows, pigs, mice, rats and primates, including humans. The preferred patient is a human.

The term "treat" refers to reducing the amount of platelet aggregation in the blood of the patient. It also refers to the management and care of a mammalian subject, preferably human, for the purpose of combating the disease, condition or disorder, resulting from platelet aggregation and includes the administration of a compound of the present invention to prevent or delay or reduce the likelihood of the onset of the symptoms or complications, alleviating the symptoms or complications or eliminating the disease, condition or disorder caused by or resulting therefrom. Examples of such diseases include coronary disease, cardiovascular disease, or peripheral vascular diseases such as ischemia, stroke, and heart attack and the like.

As used herein, the term "prophylaxis", "prevent" or synonym thereto refers to reducing the risk of a patient who is prone to or at a risk of having its platelets aggregate in the bloodstream and/or of contracting a disease or medical condition resulting from excessive platelet aggregation. Examples of such diseases include coronary disease, cardiovascular disease, peripheral vascular disease, such as ischemia, stroke and heart attack and the like.

As described hereinabove, the acetylated hydroxy containing amino acids and peptides of the present invention are useful for reducing the amount of platelet aggregation in the blood. As a result, they are each useful for treating and preventing those diseases or conditions resulting from platelet aggregation, such as those described hereinabove. They are thus useful for treating and/or preventing thrombosis, embolism, coronary diseases, cardiovascular diseases, peripheral vascular diseases and the like, such as stroke, heart attack, ischemia and the like.

Moreover, the compounds of the present invention are useful in reducing the risk of a patient suffering from or being afflicted with a disease or condition caused by or resulting from excessive platelet aggregation in the blood. They also reduce the amount of platelet aggregation in the bloodstream and thus prevent and/or retard additional platelets to aggregate in the bloodstream.

Without wishing to be bound, it is believed that the platelets adhere to the side walls of the blood vessels. If present in sufficient concentration, they can retard the blood flow in the arteries, depending on the amount of platelets present and the diameter of the arteries. If present in sufficient amounts, they can cause occlusions in vital arteries, such as coronary arteries or arteries, leading to the heart or brain, resulting in heart attacks, ischemia, or stroke. Alternatively, this may cause thrombosis or embolism. Without wishing to be bound, it is believed that the compounds of the present invention inhibit the adhesion of the platelets to the damaged walls of the arteries, increase the potency of prostacyclin and/or cause vasodilatation. Thus, the compounds of the present invention are not only useful for treating these diseases but also reduce the risk of a mammal from suffering from these diseases.

Surprisingly, all these O-acetylated derivatives of the present invention are virtually non-toxic, in contrast to the currently available anti-platelet drugs in the market. Hence they are ideal candidates as nutritional supplements, and the patient can self diagnose and self-administer these supplements with no additional medical expenditure.

Moreover, they will typically increase the blood clotting time, or platelet aggregation time and/or bleeding time in a mammal by at least 20% more than untreated individual, thus affording protection against a number of vascular diseases.

The compounds of the present invention may be used above or in combination with each other or with other drugs. When used in combination with other drugs, the administration of the drugs may be simultaneous, or sequential. Simultaneous administration includes the administration of a single dosage form that comprises all of the dosage forms at substantially the same time. Sequential administration includes the administration of at least two compounds according to different schedules provided that there is an over lay in the periods during which the treatment whether therapeutic and/or prophylactic is provided.

As used herein the term "active compound" or like term or synonym thereto refers to the acetylated hydroxy containing naturally occurring amino acids or dipeptide, as defined herein.

In addition, the term "acetylated hydroxy containing naturally occurring amino acids" or "acetylated amino acid" or like term or synonymous term refers to an amino acid which is naturally occurring containing one or more hydroxy groups on the side chain, and wherein at least one of the hydroxy groups is acetylated.

Further, the term "diacetylated hydroxy containing peptide" or "diacetylated dipeptide" or a "dipeptide" of an acetylated hydroxy amino acid herein or synonymous term refers to a dipeptide of two amino acids having at least one hydroxy group on the side chain and more preferably each has only one hydroxy group on the side chain which is acetylated. Further, at least one of the hydroxy groups on either amino acid in the dipeptide is acetylated, and more preferably a hydroxy group on each of the amino acids of the dipeptides is acetylated. In a preferred embodiment, each amino acid has only one hydroxy group on the side chain and both are preferably acetylated. The acetylated amino acids in the dipeptide may be the same or different.

The term "acetylated hydroxy containing peptide" or synonymous term refers to a peptide of two or more amino acids having at least one hydroxy group on the side chain and more preferably each of the hydroxy groups on the side chain is acetylated.

However, the preferred acetylated amino acids from which the peptide is prepared are acetylated Threonine, acetylated hydroxyproline, acetylated tyrosine and acetylated serine and acetylated carnitine.

An amino acid is a compound, which contains an amino group, which may be present as a primary amine, a secondary amine or a tertiary amine or in quaternary amino acid a carboxy group or salt thereof. The amino acid preferably contains at least one asymmetric center, which contains the side chain, which is either a hydroxy group or contains a hydroxy group. This carbon atom at the asymmetric center is preferably in the L-configuration.

An α amino acid, by definition, is a group of the formula

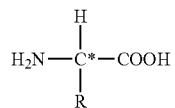

or its acidic or basic form or zwitterionic form, where the R group is the side chain of the amino acid. It is preferred that the amino acid is a α-amino acid.

When referring to the L-isomer of an α-amino acid, it to be understood to refer to the stereochemistry at the asymmetric carbon depicted hereinabove, i.e., the carbon with the asterisk. The active compound may have other asymmetric carbons present thereon, which also may exist in other sterochemical configurations at these other asymmetric carbons. All of the other stereoisomers are contemplated to be with the scope of the present invention.

As used herein, unless indicated to the contrary the term "or" refers to the disjunctive. Further, the "and" herein includes both the conjunctive and disjunctive.

Unless indicated to the contrary, the singular, as used herein, shall include the plural and vice versa.

The following non-limiting examples further illustrate the present invention:

Example 1

Anti-Platelet Activity of Acetyl Serine and Acetyl Tyrosine in Rats

A Test Method was developed to determine clotting time to evaluate the anti platelet aggregation effect of O-acetyl-L-Serine HCl salt (OAS), and O-acetyl-L-Tyrosine (OAT) by employing a capillary tube method using Swiss Albino Rats as the test system.

Young 5-6 weeks old Swiss Albino rats weighing about 200 Gm were used in the following protocol. They were obtained from an established animal supplier.

Dosage Details
1. Dose Strength: 10, 20, 50 and 100 mg/kg of OAS and OAT
2. Dose Duration: Once
3. Route of Administration: Single exposure by oral gavage.
4. No. of animals per group: 5
5. Blank Control Vehicle
  Experimental Procedure:

The rats were fasted for 18-20 hours before dosing. A Syringe attached to a 16 gauge blunt tipped canula was used for this purpose. Two hours after dosing, the animals were provided with feed. 24 hours (±10 minutes) after the administration of the drug, blood samples were collected (0.2 ml approx) in capillary tubes. Animals were anaesthetized by mild ether inhalation by keeping a cotton swab soaked in ether near the nostrils of the animal. Blood was collected from the orbital sinus onto the capillary tube. Clotting time was observed in the interval of 30 seconds. For the confirmation of clotting, clotting was checked 30 seconds after the last observed clotting. An increase in clotting time compared to vehicle is an index of inhibition of platelet aggregation.

With respect to OAT, clotting time was determined once at 2 hours after dosing and then again at 24 hours after dosing. With OAS, only one clotting time measurement, at 2 hours post dosing, was performed.

The results on the tests are shown in the table hereinbelow:

1. OAT Study

| Animal ID | Test group | Sex | Initial body weights (Fasting) | Start of bleeding time After 4 hrs of administration | Clotting time After 4 hrs of administration | In minutes | Start of bleeding time After 24 hrs of administration | Clotting time After 24 hrs of administration | In minutes |
|---|---|---|---|---|---|---|---|---|---|
| APA 211401 | Group-1 | M | 123 | 2:38 | 2:45 | 7 | 10:40 | 10:46 | 6 |
| APA 211402 | Group-1 | M | 144 | 2:39 | 2:45 | 6 | 10:41 | 10:48 | 7 |
| APA 211403 | Group-1 | M | 154 | 2:40 | 2:47 | 7 | 10:42 | 10:49 | 7 |
| APA 211404 | Group-1 | M | 160 | 2:41 | 2:48 | 7 | 10:43 | 10:50 | 7 |
| APA 211405 | Group-1 | M | 164 | 2:42 | 2:49 | 7 | 10:44 | 10:51 | 7 |
| APA 221406 | Group-2 | M | 132 | 2:45 | 2:53 | 8 | 10:46 | 10:54 | 8 |
| APA 221407 | Group-2 | M | 144 | 2:47 | 2:55 | 8 | 10:47 | 10:56 | 9 |
| APA 221408 | Group-2 | M | 156 | 2:48 | 2:57 | 9 | 10:48 | 10:55 | 7 |
| APA 221409 | Group-2 | M | 160 | 2:49 | 2:59 | 10 | 10:49 | 10:57 | 8 |
| APA 221410 | Group-2 | M | 174 | 2:50 | 2:59 | 9 | 10:50 | 10:59 | 9 |
| APA 231411 | Group-3 | M | 140 | 3:00 | 3:09 | 9 | 10:52 | 11:01 | 9 |
| APA 231412 | Group-3 | M | 144 | 3:01 | 3:11 | 10 | 10:53 | 11:03 | 10 |
| APA 231413 | Group-3 | M | 158 | 3:02 | 3:12 | 10 | 10:54 | 11:02 | 8 |
| APA 231414 | Group-3 | M | 162 | 3:03 | 3:12 | 9 | 10:55 | 11:05 | 10 |
| APA 231415 | Group-3 | M | 176 | 3:04 | 3:19 | 15 | 10:56 | 11:07 | 11 |
| APA 241416 | Group-4 | M | 140 | 3:05 | 3:23 | 18 | 10:57 | 11:11 | 14 |
| APA 241417 | Group-4 | M | 146 | 3:06 | 3:25 | 19 | 10:58 | 11:14 | 16 |
| APA 241418 | Group-4 | M | 158 | 3:07 | 3:24 | 17 | 10:59 | 11:15 | 16 |
| APA 241419 | Group-4 | M | 162 | 3:09 | 3:26 | 17 | 11:00 | 11:14 | 14 |
| APA 241420 | Group-4 | M | 176 | 3:10 | 3:29 | 19 | 11:01 | 11:15 | 14 |
| APA 251421 | Group-5 | M | 142 | 3:11 | 3:32 | 21 | 11:11 | 11:30 | 19 |
| APA 251422 | Group-5 | M | 150 | 3:12 | 3:38 | 26 | 11:12 | 11:35 | 23 |
| APA 251423 | Group-5 | M | 158 | 3:13 | 3:34 | 21 | 11:14 | 11:36 | 22 |
| APA 251424 | Group-5 | M | 162 | 3:14 | 3:43 | 29 | 11:15 | 11:40 | 25 |
| APA 251425 | Group-5 | M | 184 | 3:15 | 3:40 | 25 | 11:16 | 11:40 | 24 |

2. OAS Study

| Animal ID | Test group | Sex | Initial body weights (Fasting) | Start of bleeding time | Clotting time | In minutes |
|---|---|---|---|---|---|---|
| APA 211301 | Group-1 | M | 134 | 12:52 PM | 12:59 | 7 |
| APA 211302 | Group-1 | M | 150 | 1:00 pm | 1:07 | 7 |
| APA 211303 | Group-1 | M | 148 | 1:08 PM | 1:15 | 7 |
| APA 211304 | Group-1 | M | 164 | 1:09 PM | 1:15 | 6 |
| APA 211305 | Group-1 | M | 172 | 1:10 PM | 1:17 | 7 |
| APA 221306 | Group-2 | M | 142 | 1:19 PM | 1:25 | 6 |
| APA 221307 | Group-2 | M | 148 | 1:20 PM | 1:26 | 6 |
| APA 221308 | Group-2 | M | 152 | 1:21 PM | 1:29 | 8 |
| APA 221309 | Group-2 | M | 164 | 1:22 pm | 1:31 | 9 |
| APA 221310 | Group-2 | M | 158 | 1:23 PM | 1:32 | 9 |

-continued

| Animal ID | Test group | Sex | Initial body weights (Fasting) | Start of bleeding time | Clotting time | In minutes |
|---|---|---|---|---|---|---|
| APA 231311 | Group-3 | M | 144 | 1:26 PM | 1:35 | 9 |
| APA 231312 | Group-3 | M | 150 | 1:28 PM | 1:37 | 9 |
| APA 231313 | Group-3 | M | 158 | 1:29 PM | 1:38 | 9 |
| APA 231314 | Group-3 | M | 160 | 1:31 PM | 1:39 | 8 |
| APA 231315 | Group-3 | M | 176 | 1:33 PM | 1:41 | 8 |
| APA 241316 | Group-4 | M | 146 | 1:34 PM | 1:53 | 19 |
| APA 241317 | Group-4 | M | 148 | 1:35 PM | 1:55 | 20 |
| APA 241318 | Group-4 | M | 154 | 1:36 PM | 1:52 | 16 |
| APA 241319 | Group-4 | M | 166 | 1:38 PM | 1:55 | 17 |
| APA 241320 | Group-4 | M | 176 | 1:40 PM | 1:55 | 15 |
| APA 251321 | Group-5 | M | 148 | 1:42 PM | 2:08 | 26 |
| APA 251322 | Group-5 | M | 148 | 1:43 PM | 2:05 | 22 |
| APA 251323 | Group-5 | M | 152 | 1:44 PM | 2:10 | 26 |
| APA 251324 | Group-5 | M | 168 | 1:45 PM | 2:15 | 30 |
| APA 251325 | Group-5 | M | 182 | 1:47 PM | 2:15 | 29 |

The plot of the Log Dose vs. Clotting time in min. is depicted in FIG. 1.

In FIG. 1, the clotting time in minutes was plotted against Log of the dose in mg/kg, each point being an average of clotting time obtained in 5 rats. A value of zero was assigned to vehicle control (zero dose). As shown by the plot in FIG. 1, statistically significant ($P<0.5$) clotting times were observed at all dose levels, and between the dose levels. (AceTyro=O-Acetyl-L-Tyrosine and AceSer=O-Acetyl-L-Serine HCl).

Example 2

Human Clinical Trials with O-Acetyl Tyrosine

A Test Method was developed to determine clotting time to evaluate the anti-platelet aggregation effect of O-acetyl-L-Tyrosine (OAT) by employing capillary tube method in two human volunteers.

Two males ages 46 and 50 each weighing about 60 Kg and 90 Kg, respectively were treated according the following regimen:

Dosage Details

1. Dose Strength: Volunteer 1 (90 Kg) 1000 mg, Volunteer 2 (60 Kg) 350 mg of OAT
2. Dose Duration: Once
3. Route of Administration: Single exposure by oral gavage.
4. Blank Control Self, time zero clotting time The results are shown in the following table:

| Product O-Acetyl Tyrosine | | | |
|---|---|---|---|
| Dose = Time | 1000 mg Vol 1 | Time | 350 mg Vol 2 |
| 0 | 6 | 0 | 5.5 |
| 8 | 6.5 | 2 | 5.5 |
| 12 | 8.5 | 5 | 6 |
| 24 | 8 | 11 | 6.75 |
| 48 | 7.5 | 22.5 | 6.5 |
| Max % Increase | 42 | | 23 |
| Sustained Increase % | 25 | | 18 |

Figure 2:
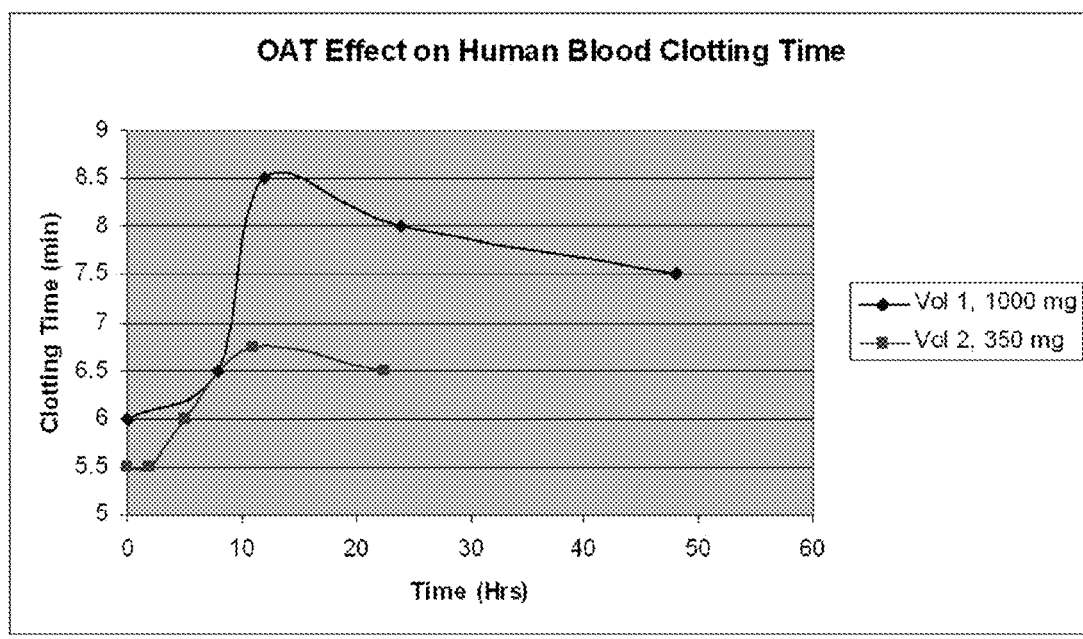
FIG. 2 depicts graphically the effect of the acetyl ester of tyrosine on human blood clotting time at different dose levels of the drug, 1000 mg, and 350 mg.

FIG. 2 plots the whole blood clotting time in the two human volunteers who took each 1000 and 350 mg. Maximum clotting time increase of 42% was seen in Vol. 1 user, who took a higher dose, and maintained 23% increase in clotting time even at 48 hours after initial dose; the second volunteer had lesser maximum and sustained increase in clotting time (25 and 18% respectively) consistent with lower dose administered.

Based upon the data shown in Table 2 and FIG. 2, it is surprising that a simple acetylated amino acid such O-Acetyl Tyrosine demonstrated dose dependent increase in clotting time, and furthermore, such increase in clotting time was sustained for at least 48 hours as measured in Volunteer 1. Neither volunteer reported any unusual side effects or toxic reactions to O-Acetyl-L-Tyrosine.

The above description illustrates the scope and spirit of the present invention. It will make apparent to those skilled in the art other embodiments. These other embodiments are within the contemplation of the present invention. Therefore, the present invention should be limited only by the appended claims.

What is claimed is:

1. A method of reducing platelet aggregation in a mammal, which comprises administering to said mammal a platelet inhibiting effective amount of an acetylated hydroxy containing naturally occurring amino acid selected from the group consisting of O-acetyl-L-hydroxyproline, O-acetyl-L-threonine, O-acetyl-L-serine, O-acetyl-L-tyrosine and O-acetyl-L-carnitine or pharmaceutically acceptable salt thereof or Zwitterion thereof.

2. The method according to claim 1 wherein the acetylated hydroxy containing naturally occurring amino acid is substantially enantiomerically pure.

3. The method according to claim 1 wherein the acetylated hydroxy containing naturally occurring amino acid is substantially pure.

4. A method of treating a condition resulting from or caused by excessive platelet aggregation in a mammal which comprises administering to said mammal in need of treatment a pharmaceutically effective amount of an acetylated hydroxy containing naturally occurring amino acid selected from the group consisting of O-acetyl-L-hydroxyproline, O-acetyl-L-threonine, O-acetyl-L-serine, O-acetyl-L-tyrosine and O-acetyl-L-carnitine or pharmaceutically acceptable salt thereof or Zwitterion thereof.

5. The method according to claim 4 wherein the condition is a vascular disease, a coronary disease or a peripheral vascular disease.

6. The method according to claim 4 wherein the condition is a stroke, heart attack or thromboembolism or ischemia.

7. A method of enhancing the cardiovascular health of a mammal, which comprises administering to said mammal a platelet inhibiting effective amount of an acetylated hydroxy containing naturally occurring amino acid selected from the group consisting of O-acetyl-L-hydroxyproline, O-acetyl-L-threonine, O-acetyl-L-serine, O-acetyl-L-tyrosine and O-acetyl-L-carnitine or pharmaceutically acceptable salt thereof or Zwitterion thereof.

8. The method according to claim 1 or 4 wherein said acetylated hydroxy containing naturally occurring amino acid or pharmaceutically acceptable salt thereof or Zwitterion thereof is administered intravenously, intraarterially, intraperitoneally, intrathecally, intraventricularly, intraurerthrally, intrasternally, intracranially, intramuscularly or subcutaneously.

9. The method according to claim 1 wherein said acetylated hydroxy containing naturally occurring amino acid or pharmaceutically acceptable salt thereof or Zwitterion thereof is administered in unit dosage form.

10. method according to claim 4 wherein said acetylated hydroxy containing naturally occurring amino acid or pharmaceutically acceptable salt thereof or Zwitterion thereof is administered in unit dosage form.

11. The method according to claim 7 wherein said acetylated hydroxy containing naturally occurring amino acid or pharmaceutically acceptable salt thereof or Zwitterion thereon is administered in unit dosage form.

12. The method according to claim 7 wherein said acetylated hydroxy containing naturally occurring amino acid or pharmaceutically acceptable salt thereof or Zwitterion thereof is administered intravenously, intra-arterially, intraperitoneally, intrathecally, intraventricularly, intraurerthrally, intrasternally, intracranially, intramuscularly or subcutaneously.

13. The method according to claim 1 wherein mammal is human.

14. The method according to claim 4 wherein mammal is human.

15. The method according to claim 7 wherein mammal is human.

16. The method according to claim 7 wherein the acetylated hydroxy containing naturally occurring amino acid is substantially enantiomerically pure.

17. The method according to claim 7 wherein the acetylated hydroxy containing naturally occurring amino acid is substantially pure.

18. The method according to claim 4 wherein the acetylated hydroxy containing naturally occurring amino acid is substantially enantiomerically pure.

19. The method according to claim 4 wherein the acetylated hydroxy containing naturally occurring amino acid is substantially pure.

20. The method according to any one of claim 1, 4 or 7, in which the acetylated hydroxy containing naturally occurring amino acid selected from the group consisting of O-acetyl-L-hydroxyproline, O-acetyl-L-threonine, O-acetyl-L-serine, O-acetyl-L-tyrosine and O-acetyl-L-carnitine or pharmaceutically acceptable salt thereof or Zwitterion thereof is administered orally, parentally, vaginally, rectally or bucally.

* * * * *